United States Patent [19]

Panunto

[11] Patent Number: 4,990,616

[45] Date of Patent: Feb. 5, 1991

[54] ZINC STEARATE AS A FLOW PROMOTING ADDITIVE FOR TRIETHYLENEDIAMINE

[75] Inventor: Thomas W. Panunto, Telford, Pa.

[73] Assignee: Air Products and Chemicals, Inc., Allentown, Pa.

[21] Appl. No.: 324,846

[22] Filed: Mar. 17, 1989

[51] Int. Cl.$^5$ .................. B01J 2/30; C07D 487/08
[52] U.S. Cl. ..................... 544/351; 252/384
[58] Field of Search ......................... 544/351

[56] References Cited

U.S. PATENT DOCUMENTS

| | | | |
|---|---|---|---|
| 3,560,414 | 2/1971 | Miskel, Jr. | 521/57 |
| 3,779,821 | 12/1973 | Fujiki | 149/46 |
| 3,834,955 | 9/1974 | Fox | 149/44 |
| 4,196,095 | 4/1980 | Cala | 252/384 |
| 4,306,994 | 12/1981 | Ellslager | 252/384 |
| 4,591,452 | 5/1986 | Worschech | 252/384 |

FOREIGN PATENT DOCUMENTS 0209720 1/1987 European Pat. Off. .

OTHER PUBLICATIONS

Shell, Chem. Abs. 89, 111663 (1977).
Hosokawa, Chem. Abs. 108, 10-15-87.

*Primary Examiner*—Mark L. Berch
*Attorney, Agent, or Firm*—Michael Leach; James C. Simmons; William F. Marsh

[57] ABSTRACT

A flowable triethylenediamine composition containing 200 to 1,000 ppm zinc stearate. Aqueous solutions containing such flowable triethylenediamine in amounts suitable for making polyurethane foam are clear and colorless without foam formation on the solution surface.

6 Claims, No Drawings

ZINC STEARATE AS A FLOW PROMOTING ADDITIVE FOR TRIETHYLENEDIAMINE

TECHNICAL FIELD

The invention relates to triethylenediamine crystal and, more particularly, relates to powdery triethylenediamine crystal containing a flow control additive.

BACKGROUND OF THE INVENTION

Triethylenediamine (TEDA), also known as 1,4-diazabicyclo(2.2.2)-octane, is well known in the commercial market as a catalyst or co-catalyst in the production of polyurethane plastics, elastomers and foams. A number of methods are known in the art for preparing and isolating this compound as a product of commercially acceptable purity.

Typically, the TEDA is isolated from the reaction mixture as a white crystalline hygroscopic product containing a small amount of by-product amine compounds. The TEDA product is generally placed on the market for commercial users in drums of about 25 kg capacity.

With improved purification the synthesized TEDA product is recovered having less than about 500 ppm by-product organic amine impurities. It was found, however, that the purified commercial powdery crystalline TEDA product of this desired low content of organic amine impurities, when stored in commercial size drums for even short periods, particularly in a moderately warm environment, tended to develop a caking, or blocking problem. This bulk aggregation of the powdery crystals is believed the result of two factors, namely, (1) sublimation and crystallization of the TEDA molecules forming a bridge between adjacent particles and (2) hygroscopicity which also results in agglomeration of adjacent particles. This stored powdery product becomes very difficult to remove from the drum by pouring or scooping.

EP 0 209 720 A1 discloses that the flowability of stored TEDA is improved by admixing with a flow promoting amount of a salt, amide or ester derivative of a $C_8$-$C_{22}$ fatty acid. Especially suitable flow promoting additives for TEDA are salts of stearic acid, particularly sodium stearate.

However, it has been discovered that such TEDA compositions containing sodium stearate at flow promoting levels (250 ppm), when dissolved in water with agitation, yield a foam on the solution surface.

Since the most common means of using TEDA as a catalyst in polyurethane and/or polyisocyanurate formulations is as a solution in water which is a blowing agent, it is of critical importance for customer acceptance of the TEDA product, that the resulting aqueous solution be a substantially clear, colorless solution. Since TEDA by itself will yield a clear, colorless, foamless solution, the customer will accept nothing less from a TEDA product containing a flow promoting additive. Foam on the surface of an aqueous TEDA solution may indicate to customers that the TEDA composition may adversely affect the polyurethane reaction or the final product.

SUMMARY OF THE INVENTION

The present invention provides a flowable triethylenediamine (TEDA) composition containing as a flow promoting additive, 200 to 1,000 ppm zinc stearate. TEDA compositions containing zinc stearate as a flow promoting additive demonstrate excellent flowability and there is no foam observed when aqueous solutions of zinc stearate-treated TEDA are prepared.

DETAILED DESCRIPTION OF THE INVENTION

As a flow promoting additive, the zinc stearate may be admixed with the TEDA crystalline powder in any manner effective to obtain good dispersion throughout the mass. The admixing may be performed at a temperature ranging from ambient up to the melting point of the TEDA powder.

A flow promoting amount of the zinc stearate is mixed with the TEDA powder, such as 0.02 to 0.1 parts by weight of zinc stearate per 100 parts of TEDA. i.e., 200 to 1,000 ppm. It is preferred that 200 to 300 ppm zinc stearate be used. At less than about 200 ppm, the zinc stearate does not afford the requisite flowability and at more than about 1000 ppm, no additional advantage is achieved.

In the following examples the flowability of TEDA was tested and rated as follows:

TEDA not treated with flow additive was added to the stainless steel mixing bowl of a Hobart dough mixer. An appropriate amount of zinc stearate was then added to the mixing bowl and the TEDA/zinc stearate blend was mixed for 1-1.25 hrs at 139 gyrations per minute (second speed level) to ensure even dispersal of the stearate flow additive throughout the TEDA.

Samples of the zinc stearate treated TEDA were placed in 16 oz. glass bottles with foil lined caps. The TEDA samples were poured, with the aide of a powder funnel, into the bottles until a depth of 5 inches had been reached; no additional force or pressure was used to increase the quantity of sample in the bottles. In each study four identical samples were bottled. These were stored at room temperature (22-26° C.). Standards were prepared by mixing untreated TEDA in the Hobart mixer, to ensure similar crystal size, and then bottled and aged along with the treated TEDA samples.

The flow properties of stored TEDA samples were measured by driving a stainless steel spatula into the sample with approximately equivalent pressure in each case. The depth of the insertion was then recorded.

The flowability was rated as follows:

Poor—Spatula penetration no more than 10% of available distance

Good—Spatula penetration from 75-99% available distance

Excellent—Spatula easily driven to bottom of sample-100% penetration

EXAMPLE 1

In this example TEDA crystalline powder containing the indicated levels of sodium stearate and zinc stearate were evaluated for their flowability properties after storage at room temperature for 3 and 7 days. Table 1 presents the results.

TABLE 1

| | Flowability of TEDA (3 days/7 days) | |
|---|---|---|
| PPM | Na Stearate | Zn Stearate |
| 50 | Poor/Poor | Poor/Poor |
| 100 | Poor/Poor | Poor/Poor |
| 250 | Good/Good | Excellent/Good |
| 500 | Excellent/Excellent | Excellent/Excellent |

TABLE 1-continued

| | Flowability of TEDA (3 days/7 days) | |
|---|---|---|
| PPM | Na Stearate | Zn Stearate |
| 1000 | Excellent/Excellent | Excellent/Excellent |

It can be seen that at least about 200 ppm zinc stearate is needed to provide the TEDA powder with acceptable flowability.

EXAMPLE 2

In this example TEDA compositions containing sodium stearate and zinc stearate at various levels were dissolved in water to provide 25 wt% solutions which were agitated and observed for foam formation on the surface of the solution. Table 2 presents the results:

TABLE 2

| | Foaming of TEDA Solution | |
|---|---|---|
| PPM | Na Stearate | Zn Stearate |
| 50 | None | None |
| 100 | Slight foam | None |
| 250 | Foam | None |
| 500 | Foam | None |
| 1000 | Foam | None |
| 1500 | Foam | None |

The advantage of zinc stearate over sodium stearate as a flow additive for TEDA is readily apparent from the absence of foam formation at all levels tested.

STATEMENT OF INDUSTRIAL APPLICATION

The invention provides for improving the flowability of stored powdery TEDA crystal by incorporation of a flow improving amount of zinc stearate. Aqueous solutions of such TEDA composition are marked by the absence of foam formation on the solution surface.

I claim:

1. In a method for improving the flowability of triethylenediamine by admixing with a stearate salt as a flow promoting additive, the improvement which comprises admixing 200 to 1,000 ppm zinc stearate.

2. The method of claim 1 in which 200 to 300 ppm zinc stearate is admixed.

3. The method of claim 1 in which about 250 ppm zinc stearate is admixed.

4. In a flowable triethylenediamine composition containing a stearate salt as a flow promoting additive, the improvement which comprises 200 to 1,000 ppm zinc stearate.

5. The composition of claim 4 which comprises 200 to 300 ppm zinc stearate.

6. The composition of claim 4 which comprises about 250 ppm zinc stearate.

* * * * *